(12) United States Patent  
Heyneker et al.

(10) Patent No.: US 6,264,891 B1
(45) Date of Patent: Jul. 24, 2001

(54) APPARATUS AND METHOD FOR CONCURRENT CHEMICAL SYNTHESIS

(75) Inventors: Herbert L. Heyneker, San Francisco; Kim D. Ha, San Jose; David K. Steinmiller, Palo Alto; Victor Simonyi, Berkeley, all of CA (US)

(73) Assignee: EOS Biotechnology, Inc., South San Francisco, CA (US)

( * ) Notice: Subject to any disclaimer, the term of this patent is extended or adjusted under 35 U.S.C. 154(b) by 0 days.

(21) Appl. No.: 09/315,363

(22) Filed: May 18, 1999

Related U.S. Application Data

(60) Provisional application No. 60/113,571, filed on Dec. 22, 1998.

(51) Int. Cl.[7] .......................... G01N 35/10; G01N 35/00
(52) U.S. Cl. ..................... 422/64; 422/63; 422/131; 422/136; 422/134; 435/6; 435/911; 435/91.2; 436/43; 436/47; 436/174; 436/177
(58) Field of Search ................... 436/43, 47, 49, 436/174, 179, 180; 422/63, 64, 81, 100, 101, 131, 136, 134; 435/6, 91.2, 91.1

(56) References Cited

U.S. PATENT DOCUMENTS

| | | |
|---|---|---|
| 4,170,625 | 10/1979 | Welch . |
| 4,221,568 | * 9/1980 | Boettger ........................ 23/230 R |
| 4,871,683 | * 10/1989 | Harris et al. .................... 436/531 |
| 5,053,454 | * 10/1991 | Judd ............................. 525/54.11 |
| 5,106,583 | 4/1992 | Raysberg et al. . |
| 5,288,468 | 2/1994 | Church et al. . |
| 5,288,514 | 2/1994 | Ellman . |
| 5,445,934 | 8/1995 | Fodor et al. . |
| 5,472,672 | 12/1995 | Brennan . |
| 5,595,707 | 1/1997 | Copeland et al. . |
| 5,639,603 | 6/1997 | Dower et al. . |
| 5,789,162 | 8/1998 | Dower et al. . |
| 5,807,525 | 9/1998 | Allen et al. . |

FOREIGN PATENT DOCUMENTS

| | | |
|---|---|---|
| 2108659 | * 5/1983 | (GB) . |
| 2 194 176B | 3/1988 | (GB) . |
| WO 9965602 | * 10/1999 | (WO) . |

OTHER PUBLICATIONS

S. Narang, Ed., *Synthesis and Applications of DNA and RNA*; Academic Press, Inc., New York (1987) Ch. 2 and 3, pp. 9–94.

* cited by examiner

Primary Examiner—Jill Warden
Assistant Examiner—Kathryn Bex
(74) Attorney, Agent, or Firm—Townsend & Townsend & Crew LLP

(57) ABSTRACT

This invention provides an apparatus for preparing chemical libraries. The apparatus includes (1) a carousel comprising a plurality of reaction mounts having at least one reaction well; (2) a rotator that rotates the carousel step-wise; (3) a fluid delivery system; (4) a drain system; and (5) a programmable computer that controls the operation of the apparatus, including the rotator, the fluid delivery system, the drain system and other systems in the apparatus. The preparation of chemical libraries involves rotating the carousel through a plurality of stations. At each station, a physical step in a reaction protocol is carried out on the reaction wells of the mount docked at the station.

31 Claims, 5 Drawing Sheets

APPARATUS AND METHOD FOR CONCURRENT CHEMICAL SYNTHESIS

CROSS-REFERENCES TO RELATED APPLICATIONS

This application claims the benefit of the priority date of U.S. Provisional Patent application No. 60/113,571, filed Dec. 22, 1998.

STATEMENT AS TO RIGHTS TO INVENTIONS MADE UNDER FEDERALLY SPONSORED RESEARCH AND DEVELOPMENT

Not applicable.

BACKGROUND OF THE INVENTION

This invention is directed to the fields of mechanical devices and methods of organic chemistry. More particularly, this invention provides a machine for preparing chemical libraries and methods of preparing those libraries.

Chemical libraries are collections of different chemical compounds, usually of the same class. Chemical libraries are useful in screening methods to determine whether any of the compounds have particular properties. Libraries of nucleic acids are particularly useful in hybridization analysis to detect the presence of target nucleic acids in a sample.

Methods in combinatorial chemistry are useful in the creation of chemical libraries. The methods usually involve adding different units sequentially to a base molecule, either randomly or by design. Apparatuses have been described that produce libraries of nucleic acids. These include, for example, U.K. Patent 2,194,176 (Nicholson), U.S. Pat. No. 5,288,468 (Church et al.), U.S. Pat. No. 5,445,934 (Fodor et al.) and U.S. Pat. No. 5,472,672 (Brennan). Improved apparatuses that increase the speed at which libraries of molecules can be made would be a useful addition to the art.

SUMMARY OF THE INVENTION

This invention provides an apparatus for preparing chemical libraries in which the members of the library are prepared in parallel, continuous reactions, rather than batch-wise. This arrangement allows more rapid synthesis of the libraries. The apparatus is especially adapted to the preparation of libraries of polymers, such as nucleic acids, polypeptides and peptide nucleic acids. The apparatus includes a rotatable carousel that contains a plurality of reaction mounts. Each reaction mount comprises at least one reaction well arranged on a radius with respect to the axis. The radii are spaced apart at equal angles so that the wells are arranged in at least one concentric circle around the axis. The apparatus also contains a rotator that rotates the carousel step-wise around the axis. Each incremental step docks each of the reaction mounts at a different reaction station where a physical step in the chemical protocol takes place. The reactions steps generally involve at least fluid delivery to a reaction well, drainage of fluid from a well, and incubation or wait (null) steps, in which fluid is neither added to nor removed from a well. Accordingly, the apparatus of this invention includes a fluid delivery system that delivers liquid to at least one reaction well in each of a plurality of docked reaction mounts and a drain system that drains liquid by differential pressure from at least one reaction well of each of a plurality of docked reaction mounts. The rotation of the carousel and the physical steps are controlled by a programmable digital computer.

The creation of chemical libraries involves the creation of chemical linkages in a parent molecule. Usually the process is iterative, generating multiple new linkages. Frequently, as is the case for polymers, the generation of a linkage involves coupling a component to the parent molecule. The creation of a chemical linkage, in turn, can be divided into a number of sequential chemical steps. For example, the creation of a phosphodiester bond in the synthesis of a nucleic acid generally involves deprotecting a sugar moiety of a parent molecule, coupling a reactive phosphoramidite to the sugar moiety, oxidizing the phosphoramidate bond into a phosphotriester bond, and capping unreacted molecules. Ultimate removal of a protecting group generates the phosphodiester. This procedure can, in turn, be broken down into the physical steps of adding liquid containing reagents or wash solutions to a reaction well containing the parent molecule, removing liquid from the well and incubating, or waiting. These physical steps are carried out at the stations designated by the apparatus. The stations are arranged in a circle around the carousel. Each station performs, in sequence, one of the physical steps of the reaction. Thus, as a reaction mount moves from station to station the set of sequential steps is performed on the wells of the reaction mount so that after one complete rotation, the entire series of steps has been performed on the reaction wells of the mount. In this way, the chemical linkage is established on the parent molecule in the well. The parent molecule is reversibly immobilized on an inserted solid support, such as glass or an inert polymer or plastic such as polystyrene, polyethylene or Teflon™ (available from, e.g., PE Biosystems). However, the reaction mounts also are arranged in a circle around the carousel. Therefore, at each incremental step, a different physical step in the process is carried out on the wells of one of the reaction mounts. Consequently, the creation of the linkages is carried out in parallel, with each reaction mount at a different stage of the reaction. Thus, the methods of this invention do not require all the reaction wells to pass through a single step in the reaction before any other reaction well can continue on the next step. This saves considerable time in the process.

The creation of a library is limited by the number of reaction wells that one can perform a physical step on at any one time. For example, if one wishes to prepare 192 different compounds, and one has the capacity to perform a physical step on eight reaction wells at a pass, it would require twenty-four passes before the next step can begin. In contrast, by performing the steps in parallel on eight wells at a time, twenty-four sets of wells are actively engaged in the chemical steps.

In one aspect this invention provides an apparatus comprising: a) a carousel that is rotatable around an axis, the carousel comprising a plurality of reaction mounts, each reaction mount comprising at least one reaction well arranged on a radius with respect to the axis, the radii spaced apart at equal angles, whereby the wells are arranged in at least one concentric circle around the axis; b) a rotator that rotates the carousel step-wise around the axis, each incremental step docking each of the reaction mounts at a separate station; c) a fluid delivery system that delivers liquid to at least one reaction well in each of a plurality of docked reaction mounts; d) a drain system that drains liquid by differential pressure from at least one reaction well of each of a plurality of docked reaction mounts; and e) a programmable digital computer that controls the rotator, the fluid delivery system and the drain system.

In one embodiment of the apparatus: (i) each reaction well comprises a drainage hole; (ii) the carousel comprises a plate which comprises a plurality of liquid conduits that connect with the drainage holes and are engagable with the drain system; and (iii) the drain system is a vacuum drain system comprising: (1) a plurality of vacuum lines that connect with vacuum source and (2) conduit engagement means that engage the vacuum lines with a plurality of the liquid conduits when the reaction mounts are docked at a station, whereby liquid in the reaction wells is drained through the vacuum lines.

In a further embodiment of the apparatus: (i) each liquid conduit comprises: (1) a depression in the plate below the reaction mount which forms a chamber with the reaction mount, wherein the chamber communicates with the drainage holes of the reaction mount; (2) an exit port exiting under the plate; and (3) a bore through the plate the connects the chamber with the exit port; and (ii) the conduit engagement means comprises: (1) a non-rotating connector plate positioned under the carousel; the connector plate having an engagement port that is engagable with the exit port positioned at each station, wherein each of a plurality of the engagement ports is connected to a vacuum line; and (2) an actuator that raises the connector plate to engage the plurality of engagement ports with the plurality of exit ports.

In a further embodiment of the apparatus the fluid delivery system comprises: (i) an assembly positioned above the carousel, the assembly comprising a plurality of dispensing modules mounted at each of a plurality of the stations, each dispensing module comprising a dispensing head adapted to deliver fluid to the well of a reaction mount docked at the station; (ii) a plurality of fluid dispensers, each dispenser adapted to dispense an amount of fluid; (iii) a plurality of fluid lines, each fluid line connecting a fluid dispenser to a dispensing head.

In another aspect this invention provides a method for performing in parallel a series of physical steps in a chemical reaction protocol, wherein the protocol generates a chemical linkage in a parent molecule. The method comprises: a) providing a carousel that is rotatable around an axis, the carousel comprising a plurality of reaction mounts, each reaction mount comprising at least one reaction well arranged on a radius with respect to the axis, the radii spaced apart at equal angles, whereby the wells are arranged in at least one concentric circle around the axis, wherein each well comprises the parent molecule attached to a solid support; b) rotating the carousel step-wise around the axis at least once, each incremental step docking each of the reaction mounts at a separate station, wherein (1) each station is dedicated to perform a physical step in the series during a docking, wherein the physical steps include adding a liquid to a well, draining a liquid from a well, and incubating; and (2) the stations are arranged to perform the series of physical steps in sequence; and c) performing, with each rotation of the carousel, the series of physical steps in a reaction well of each of at least two of the reaction mounts, whereby a chemical linkage is generated in the parent molecule.

In another aspect this invention provides a method for performing in parallel a series of physical steps in a chemical protocol. The method comprising the steps of: a) providing a carousel that is rotatable around an axis, the carousel comprising a plurality of reaction mounts, each reaction mount comprising at least one reaction well arranged on a radius with respect to the axis, the radii spaced apart at equal angles, whereby the wells are arranged in at least one concentric circle around the axis, wherein each well comprises the parent molecule attached to a solid support; b) providing a rotator that rotate the carousel step-wise around the axis, each incremental step docking the reaction mounts a station, wherein: (1) each station is dedicated to perform a physical step in the series during a docking and (2) the stations are arranged in series from an initial station that performs an initial physical step in a series of physical steps in a chemical protocol to a final station that performs a final physical step in the series of physical steps; c) performing an initial rotation of the carousel around the axis, wherein the stations begin to perform the series of physical steps as a reaction mount docks at the initial station; and d) performing a final rotation of the carousel around the axis, wherein the stations cease to perform the series of physical steps as a reaction mount docks at the final station. The initial and final rotations result in one complete series of steps on a reaction well of each reaction mount.

DESCRIPTION OF THE SPECIFIC EMBODIMENTS

I. Definitions

Figure 1:
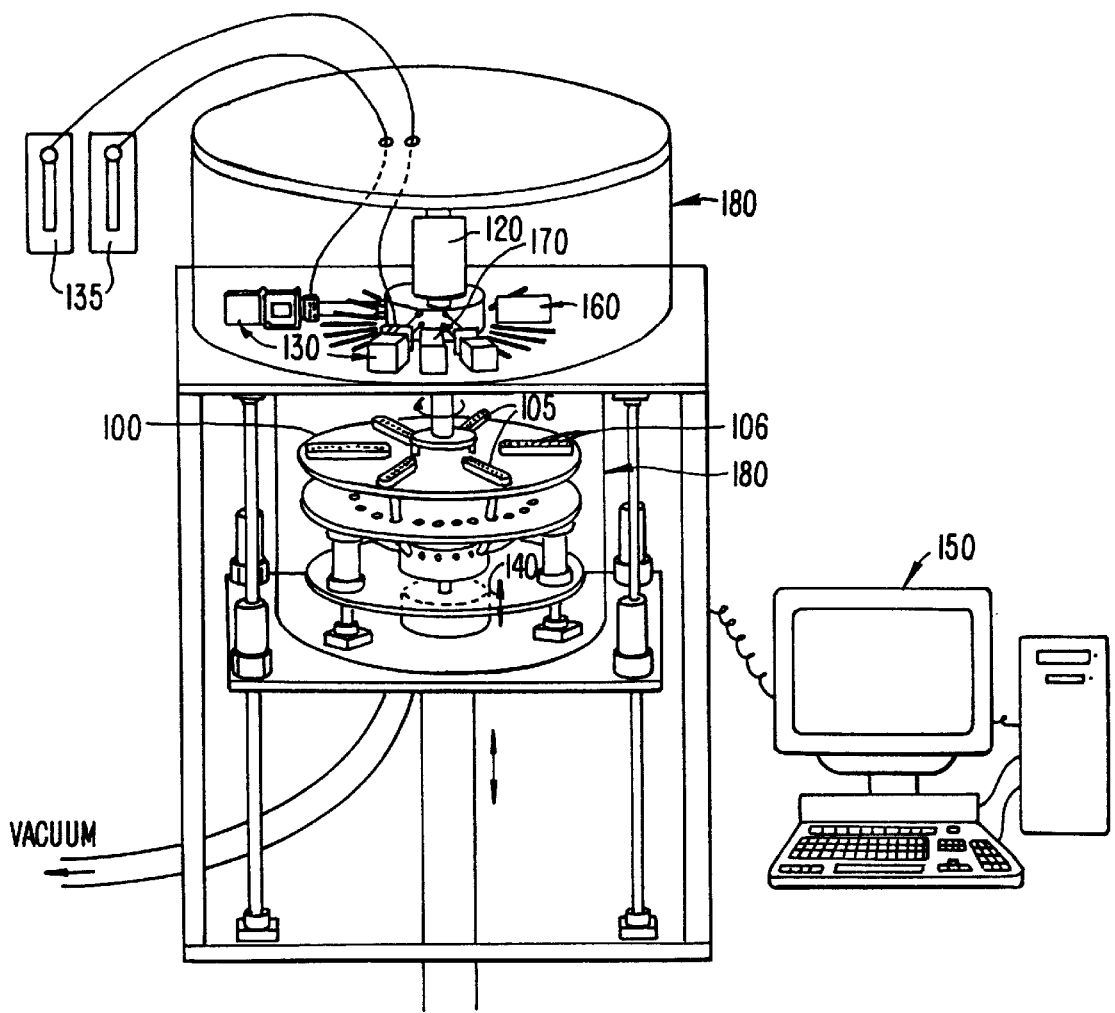
FIG. 1 depicts the apparatus of this invention.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). As used herein, the following terms have the meanings ascribed to them unless specified otherwise.

"Parent molecule" refers to a molecule bound to a solid support, including a linking group through which a first component is subsequently bound to the solid support.

"Component" refers to an atom or molecule linked to a parent molecule in a chemical reaction. In one embodiment, the component is a monomer.

"Monomer" refers to a chemical compound that can be chemically linked in iterative fashion in the generation of a polymer.

"Polymer" refers to a compound comprising a series of monomers connected through a chemical linkage. Polymers include, without limitation, nucleic acids (nucleotides joined by phosphodiester linkages), polypeptides (amino acids joined by amide linkages), polysaccharides (monosaccharides joined by glycosidic linkages), various nucleic acid analogs (e.g., peptide nucleic acids), polyurethanes, polyesters, polycarbonates, polyureas, polyamides, polyethyleneimines, polyarylene sulfides, polysiloxanes, polyimides and polyacetates.

"Scaffold molecule" refers to a parent molecule which is not a polymer. Scaffold molecules can be substituted at various positions by one or more chemical linkages with various components. Scaffold molecules also can be modified in existing chemical linkages by, e.g., oxidation or reduction. Molecules bearing a common skeleton that can function as scaffold molecules include diazepines and other small molecules, such as described in U.S. Pat. No. 5,288,514 (Ellman), hydroxystillbenes, urea linked diamines, phosphonic acid esters, beta-turn mimetics, pyrazoles, isoxazoles, miconazole analogs, aminoproline analogs, piperazinediones, hydantoins using a carbamate linker, 1-phenyl-pyrazolones, imidazoles, beta-lactams, pyrrolidines, quinolones, thiazolidines, pyridines, pyridopyryimidines, carbolines, hetrocyles, piperazines, polyazacyclophanes, quinolines and tertiary amines. (See, e.g., THE COMBINATORIAL INDEX.)

In the methods of this invention each rotation of the carousel results in one complete reaction cycle that creates a new linkage. Additional cycles create further linkages. In the case of a polymer, iteration of the process results in the addition of new moieties to the end of a growing chain. In the case of a scaffold compound, the iterative process can mean reacting a different site on the compound to create a new linkage.

"Nucleic acid" refers to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2'-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 100 nucleotides. It will be understood that when a nucleotide sequence is represented by a DNA sequence (i.e., A, T, G, C), this also includes an RNA sequence (i.e., A, U, G, C) in which "U" replaces "T."

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. The term "peptide" typically refers to short polypeptides containing from 2 to about 50 amino acids. The term "protein" typically refers to large polypeptides containing more than about 50 amino acids.

"Chemical library" refers to a collection of compounds of different structures. Generally, the compounds will fall into the same class of chemical compounds, e.g., DNA, polypeptides, benzodiazepines, etc. Libraries of compounds can be divided into two main classes. A first class is libraries of polymers. A second class is libraries of functionalized scaffold molecules. In either case, the various chemical linkages that can be created with the methods of this invention are at the discretion of the practitioner.

"Chemical linkage" refers to one or more chemical bonds having a particular chemical character. These include, without limitation, a phosphodiester bond, a phosphorothioate bond, a phosphonate bond, a phosphoramidate bond, an amide bond, an imine bond, a carbamate bond, an azo bond, a sulfone bond, a sulfonide bond, a sulfonamide bond, a sulfide bond, a disulfide bond, an ether bond, an ester bond, a thiourea bond, a urea bond and a carbon-carbon bond (single, double or triple bond).

"Plurality" means two or more.

II. Apparatus for Concurrent Chemical Synthesis

A. Operating Parts

Referring to FIG. 1, the apparatus of this invention includes (1) a carousel 100 comprising a plurality of reaction mounts 105 having at least one reaction well 106; (2) rotator 120 that rotates the carousel step-wise; (3) a fluid delivery system 130 and 135; (4) a drain system 140; and (5) a programmable computer 150 that controls the operation of the apparatus, including the rotator, the fluid delivery system, the drain system and other systems in the apparatus. Optionally, the apparatus can include a temperature controlling system 160 for regulating temperature of a reaction mount docked at a station and an optical analyzing system 170 for analyzing fluid in a well of a reaction mount docked at a station. In another embodiment, the apparatus comprises a containment system 180 that separates the carousel, drain and fluid delivery systems from the exogenous environment and allows the chemical reaction to occur in an environment of choice (e.g., $N_2$).

B. Carousel

The apparatus comprises a carousel that comprises a plurality of reaction mounts having reaction wells, in which the protocol is performed. In a preferred embodiment, the carousel comprises a circular plate 100 on which reaction mounts 105 can be mounted. In one embodiment, the plate is about 0.475 inches thick, 12 inches in diameter and is made of anodized aluminum. However, the carousel could take other configurations and materials, e.g., a hub with spokes that support the reaction mounts. The number of reaction mounts held by the carousel is not critical. However, it is very efficient to include as least as many mounts as there are physical steps in the chemical protocol. In a preferred embodiment of this invention, the carousel holds 24 reaction mounts, and the protocol includes 24 steps.

The reaction mounts generally are removably insertable onto the carousel. They can be composed of any material that resists reaction with the chemicals that are placed in the reaction wells. For example, stainless steel is an attractive material. Various plastics, such as polyethylene or polypropylene also are useful. In a preferred embodiment the mounts are approximately ¼-inch thick anodized and teflonized aluminum solid rectangular polygons of approximately 0.3-inch wide and 3.8 inches in length. These mounts will be fixed statically to the circular plate by screws at either end, positioned radially from a distance form the center of 2.5 inches out to the edge of the plate.

Figure 2:
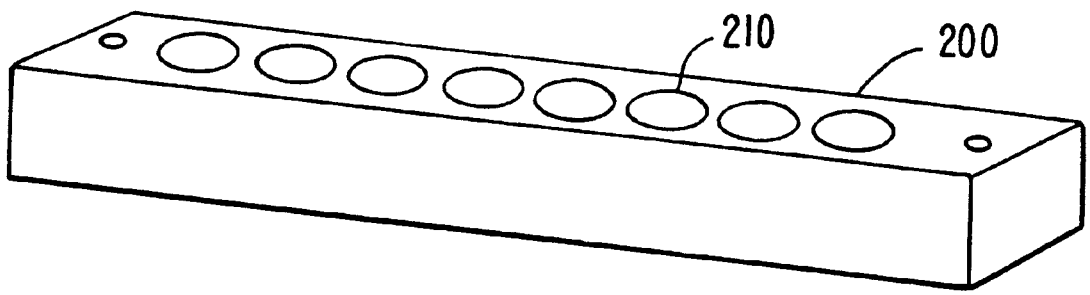
FIG. 2 depicts a reaction mount.
Figure 2:
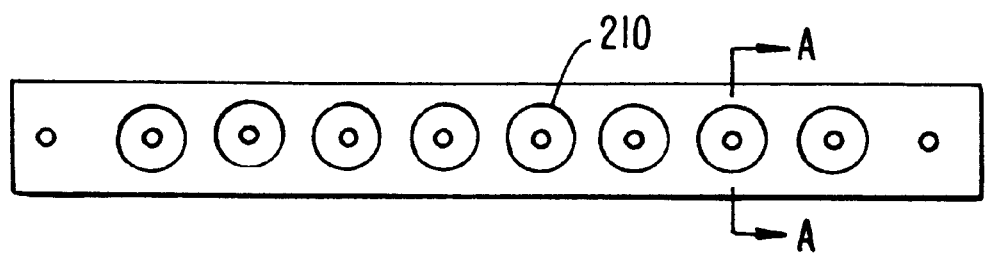
Figure 2:
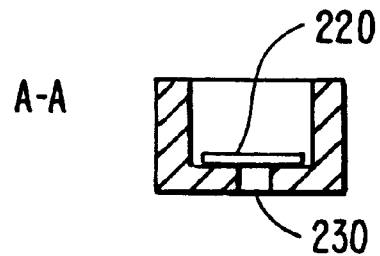

Referring to FIG. 2, reaction mount 200 includes at least one reaction well 210. The function of the reaction wells is to provide a vessel to hold a solid support 220 on which a parent molecule will be attached and to provide a volume for carrying out the reactions. In a preferred embodiment, the reaction mounts contain a plurality of reaction wells, e.g., eight wells. In general, the wells are arranged so as to be accessible to the fluid delivery and drain systems. In a preferred embodiment, the wells are arranged linearly. The line of wells is positioned along a radius of the plate, so that at each station, the fluid handling devices can work along the radius. In a preferred embodiment, each well comprises a drain hole 230 in its bottom, through which liquid can drain out of the well.

In certain embodiments, the reaction mounts of this invention can be removed from the carousel and assembled into "microtiter plates." Microtiter plates typically have a multiple of 96 wells arranged in rows and columns. For example, a 96-well plate could have 8 rows and 12 columns. A 384-well plate could have 16 rows and 12 columns. Accordingly, the number of wells on a reaction mount can be chosen to meet this arrangement, e.g., 8 wells, 12 wells, 16 wells, etc. In one embodiment, the wells of a reaction mount are configured as those in a microtiter plate, about 9 mm apart center-to-center and about 7/32" in diameter.

The wells are adapted to contain solid supports 220 on which the parent molecule is attached. The solid supports can be made of any inert material that will not react with the fluids added to the well. Inert plastics or glass are preferred. Also, it is useful to attach the parent molecule to the solid support by means of a cleavable linkage, such as succinate linker, in order to isolate the molecules from the support.

Figure 3:
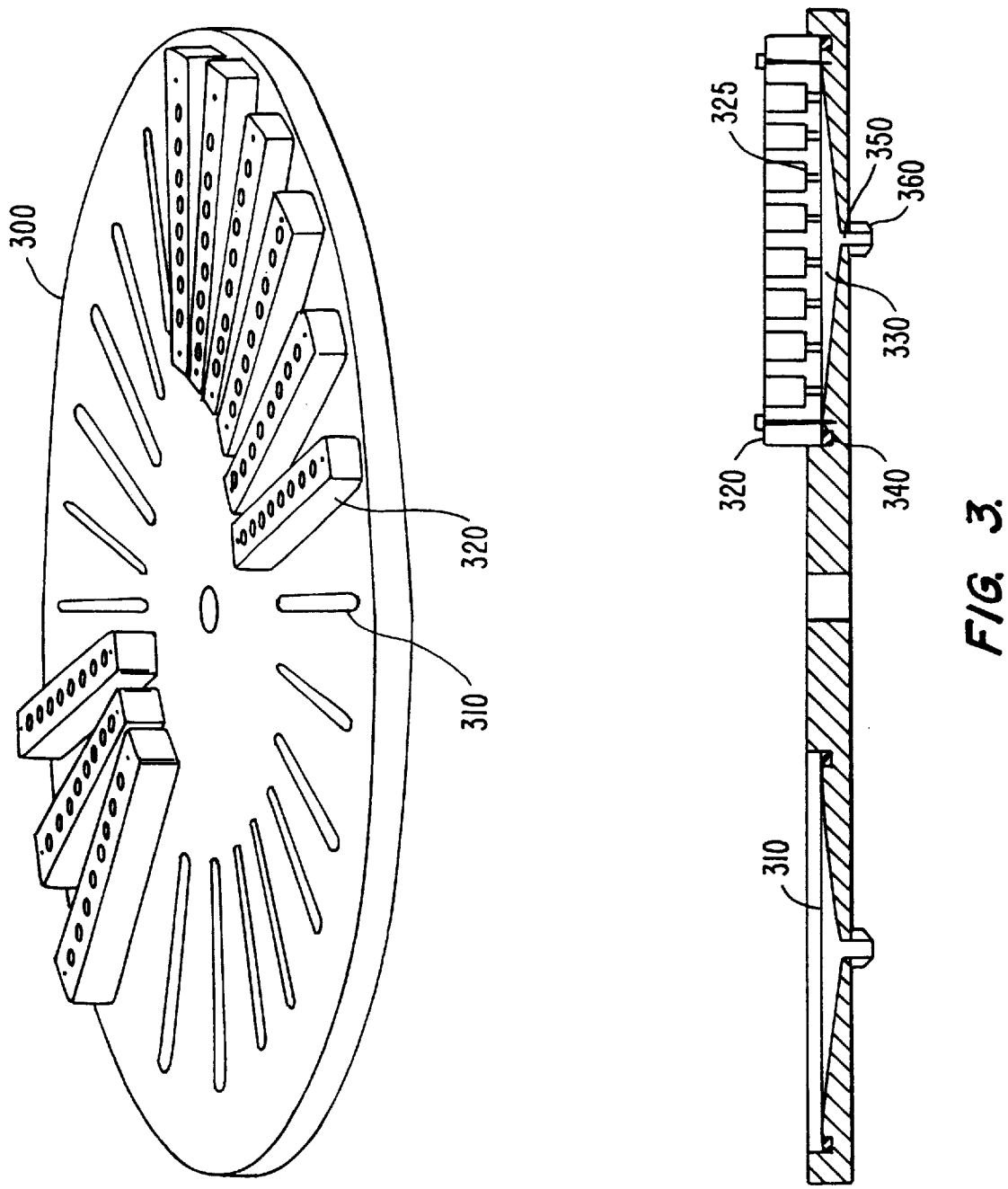
FIG. 3 depicts a carousel and liquid conduit.

In a preferred embodiment the carousel also functions to transmit liquid from the reaction wells to the drain system. The carousel transmits liquid through a series of conduits that connect holes in the reaction well with the drain system, when the drain system is engaged with the plate. Preferably, a single bore in the plate connects the drain system with all the holes in a reaction mount. Referring to FIG. 3, the carousel plate 300 comprises a depression 310 that runs horizontally the length of the mount. The bottom of reaction mount 320 covers this depression, forming a chamber 330. O-ring 340 on the bottom of the mount seals this chamber. The screws holding the mount to the plate will provide the normal force to form the seal. On the bottom of each depression is a single bore 350 through the plate. The depression itself is sloped towards the drain bore to include gravity in the forces draining the chamber. This bore through the disc terminates in exit port 360, e.g., a Teflon™ or stainless steel nipple, that serves as the connection for a vacuum drain system. Thus, liquid can be drained from a well through a hole in the well, collected into the depression in the plate and flow out through the bore in the plate.

C. Rotator

One aspect of this invention is rotating the reaction mounts through a number of stations where a step in the reaction protocol takes places. The invention provides for this purpose a rotator that rotate the carousel in a step-wise fashion through a number of incremental steps. Each step rotates the carousel a designated number of equal degrees. Thus, the rotator stops the reaction mounts at each of a number of stations defined by the stopping positions. At each station, the apparatus performs one of the physical steps in the protocol. The number of stations is selected to accommodate the number of physical steps in the protocol and the reaction mounts loaded on the carousel.

In general, the number of degrees for each step will equal 360° divided by the number of stations. For example, in one embodiment, a motor rotates the carousel through twenty-four stations in 15° steps. Alternatively, there could be 18 stations at 20° intervals, 36 stations at 10° intervals, etc.

In order to have each reaction mount stop at a station with each step, the reaction mounts must be placed around the carousel at intervals equaling a multiple of the angle between stations. For example, if the stations are set 15° apart, the reaction mounts can be stationed at 15° intervals. Alternatively, fewer reaction mounts can be placed at multiples of 15° (e.g., 12 mounts at 30° or 8 mounts at 45°) or combinations thereof, so that with each incremental step, a reaction mount stops at a station. In such cases, each step will move a mount to a station, but certain stations may be left unoccupied and will be dormant during that step.

The rotator is any rotary activator to effect a mechanical rotation including, e.g., an electromechanical motor, a pneumatic activator or hydraulic activator that functions as a microstepping stepper motor. The motor can engage the carousel through an axle. However, the motor can be connected to the carousel by other means, such as a belt or lever. In one embodiment, the motor is positioned above the plate and rotates the plate by means of an axle connecting the motor to the plate. Position feedback for the motor can be provided by an optical encoder and by IR sensor for homing.

At each station one physical step in the protocol is performed on the reaction wells of a reaction mount docked there. These steps include adding liquid to a well, draining liquid from a well and incubation or a null step. As discussed below, other steps are contemplated including incubating with heating or analysis of the materials in the well. In any case, the apparatus is adapted so that devices for fluid delivery, fluid drainage or other functions are positioned to work at the stations defined by the steps of the motor.

D. Drain System

The use of the apparatus involves draining liquid deposited in a reaction well, with or without simultaneous adding of liquid to the well (e.g., washing). Accordingly, the apparatus of this invention includes a drain system that removes liquid from the reaction wells. The drain system can drain liquid from the wells by any means. In a preferred embodiment, the apparatus is adapted to drain liquid from a hole in the bottom of the wells. This can be accomplished by gravity, but preferably, drainage is active, employing a pressure differential. This includes, preferably, a vacuum to suck liquid from the well, or over-pressure applied to the top of a well to push liquid out. In another embodiment, drainage is achieved by sucking liquid (e.g., by a tube) from the top opening of the well, to which liquid is added.

In a preferred embodiment, the drain system is a vacuum drain system that removes liquid from a hole in the bottom of a well by suction. In this embodiment, each reaction well includes a drainage hole in the bottom through which liquid can drain. The carousel plate comprises a plurality of conduits terminating, e.g., in an exit port, that connects the drainage holes to the drain system when the drain system is engaged with the carousel. More specifically, referring back to FIG. 3, each liquid conduit comprises (1) depression 310 in the plate below reaction mount 320 which forms chamber 330 with the reaction mount, wherein the chamber communicates with drainage holes 325 of the reaction mount; (2) exit port 360 exiting under the plate; and (3) bore 350 through the plate that connects the chamber with the exit port.

Figure 4:
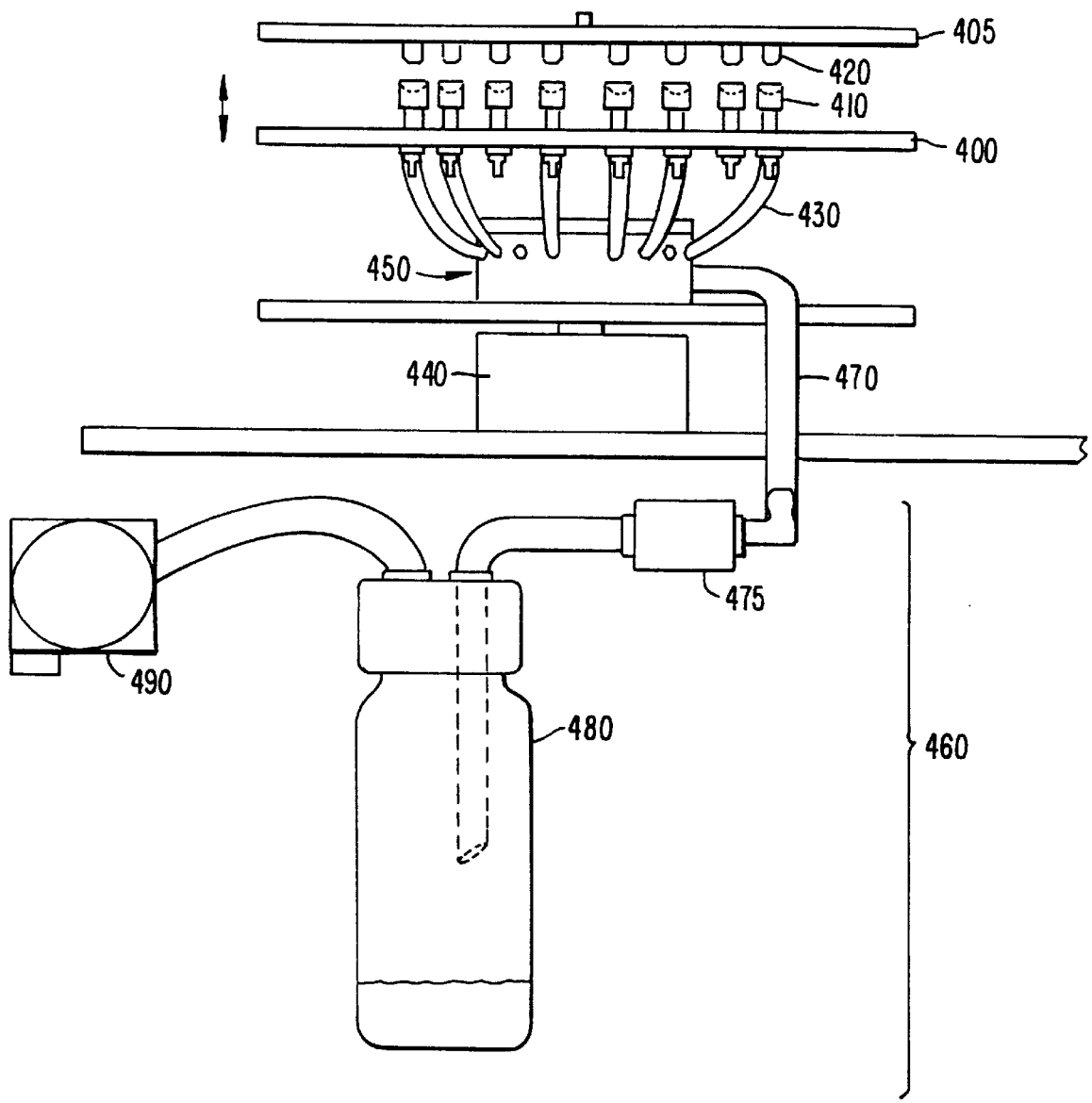
FIG. 4 depicts a drain system.

Referring to FIG. 4, the drain system can comprise conduit engagement means to engage the conduits and drain liquid from them. The conduit engagement means can comprise (1) non-rotating connector plate 400 positioned under carousel 405. The connector plate has an engagement port 410 that is engagable with the exit port 420 positioned at each station, wherein each of a plurality of the engagement ports is connected to a vacuum line 430; and (2) an actuator 440, e.g., a pneumatic cylinder, solenoid or linear motor, that raises the connector plate to engage the plurality of engagement ports with the plurality of exit ports. The exit port and the conduit engagement means preferably are complementary mechanical parts that fit each other. For example, the exit port can comprise a nipple (a hollowed protrusion) that fits with nozzles of the engagement means. This arrangement can be reversed.

The conduit engagement means, e.g., nozzles, are arranged around the connector plate at locations that correspond to the stations at which the reaction mounts will stop. For example, the nozzles can be arranged circularly at equal intervals (e.g., 15° intervals for a device with 24 stations) and at a radius placing them just below the exit ports. At each incremental step, the drain system is engaged with the carousel by raising the connector plate to engage the engagement means with the exit ports. This connection is airtight. Vacuum lines are attached to the nozzles that are at locations designated as drain stations. The other nozzles are not connected to vacuum lines, thus no draining takes places at those stations. The application of vacuum sucks the liquid from the wells. Then the connector plate is lowered to allow rotation of the carousel in the next step.

Vacuum lines 430 connect through manifold 450 with vacuum source 460, e.g., a vacuum pump or any source of vacuum that can suck liquid from the vacuum lines, and conduit engagement port 410 that engage the vacuum lines with a plurality of the liquid conduits when the reaction mounts are docked at a station. In this way, liquid in the reaction wells is drained through the vacuum lines and into a trap. From manifold 450, a tube 470 runs through a valve and to a vacuum trap 480. The trap is evacuated using vacuum pump 490 that can withstand the corrosive chemicals used in synthesis. After the cylinder raises the plate, the vacuum drain is activated by opening the valve to the trap. At the end of the drain time, this valves is closed and the plate is lowered (This can occur while the dispensing is taking place.) When the valve is open, a vacuum is created in the manifold, in the vacuum tubes, and in the depressions below the reaction mounts located at drain stations. This serves to drain the wells in those stations.

This arrangement allows great flexibility as drain stations can be moved, added, or deleted simply by connecting or disconnecting a tube from the station nozzle to the manifold.

E. Fluid Delivery System

Figure 5:
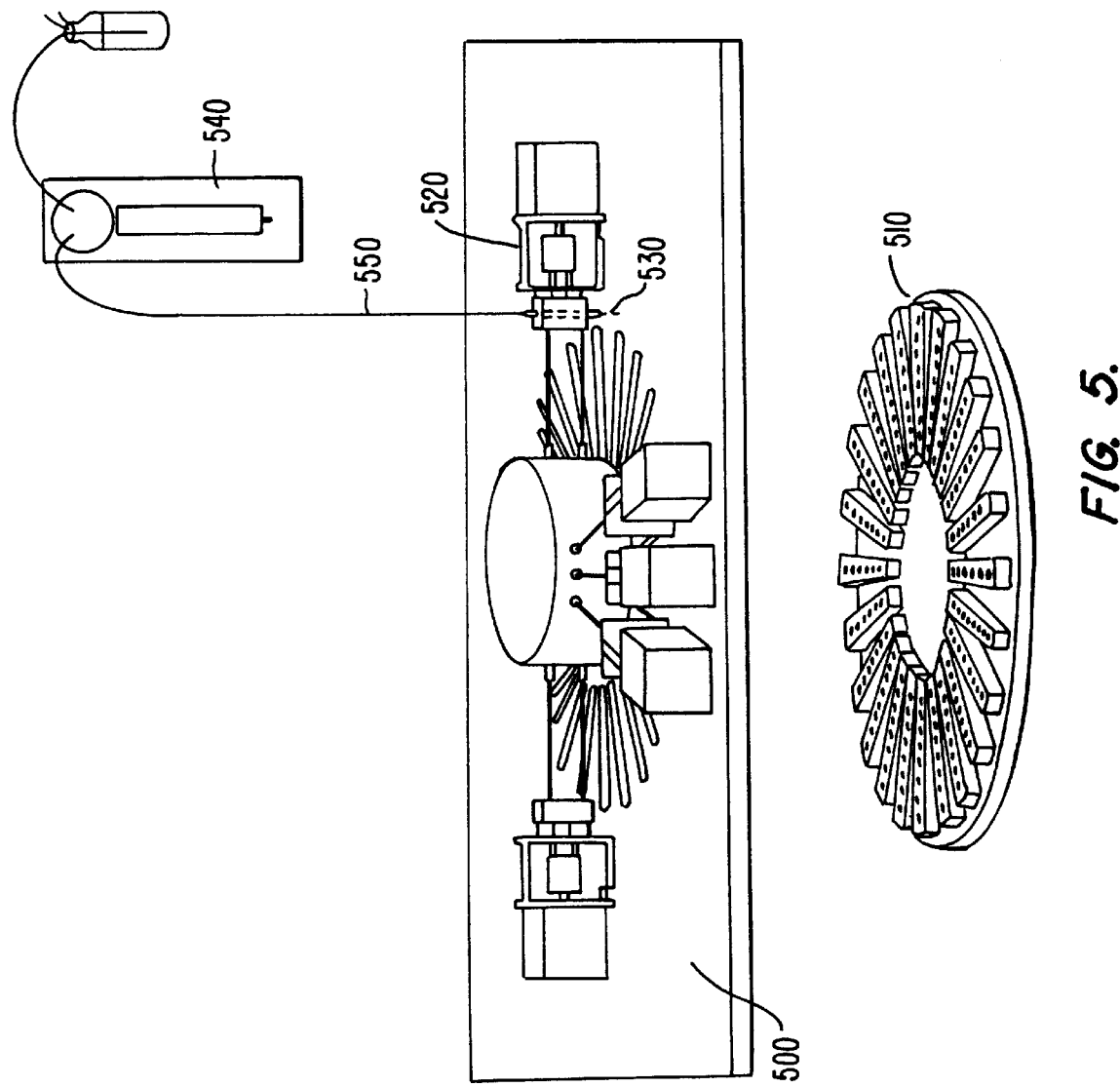
FIG. 5 depicts a fluid delivery system.

The apparatus also includes a fluid delivery system that delivers fluid to the wells of reaction mounts docked at stations designated for fluid delivery. Referring to FIG. 5, the fluid delivery system includes, in one embodiment, assembly 500 positioned above carousel 510. The assembly includes a plurality of dispensing modules 520 mounted at each of a plurality of the stations. Each dispensing module comprises a dispensing head 530 adapted to deliver fluid to the well of a reaction mount docked at the station. The fluid dispensing system also includes a plurality of fluid dispensers 540, each dispenser adapted to dispense an amount of fluid. The system also includes a plurality of fluid lines 550, each fluid line connecting a fluid dispenser to a dispensing head.

The dispensing modules can deliver liquid with positive displacement pumps. The dispensing head can include tube ends that are located above each well. Alternatively, the dispensing heads can be located above the reaction mounts and moved by, e.g., stepper motors and lead screws along the length of the reaction mounts. The motion relative to the carousel is radial (e.g., from outer diameter to inner diameter). The dispensing head stops above the center of each well in the reaction mount. If the synthesis program determines that fluid is to be added to that particular well, then the syringe pump delivers the designated volume.

For some dispensing stations, e.g., wash stations, there is a single tube end. But for there are some processes that either require multiple fluids to be dispensed concurrently or a single fluid from a choice of, e.g., four for nucleic acid synthesis. At these stations, multiple tube ends are carried along by the motor and lead screws, with all the tube ends pointing to the center of the well.

For DNA synthesis, the two stations that can have multiple dispensing are the capping stations (Cap A and Cap B need not be dispensed at the same exact moment, but are always used together) and the amidites. For the amidites, one monomer usually is dispensed out of the four at each well. However, in creating combinatorial libraries, one can deliver a mixture of amidites to each of the wells, e.g., 25% of all four, 50% of each of the purines or pyrimidines, etc. Using multiple heads saves stations for other uses. Alternatively, four separate stations can be dedicated to delivering one of each of the bases.

To change the location of a particular dispensing process, one removes the dispensing station and places it at another station, e.g., by screwing it in. Just like drain stations, moving, adding, or deleting a dispensing station is simple. Thus, changing the set of chemical additions to satisfy a different chemical synthesis protocol is easy, making this combinatorial chemistry synthesis machine extremely flexible.

F. Temperature Controlling System and Optical Analyzing System

Other processes (such as heating or analysis) can be placed at any station in the cycle. The heating process, for example, will be achieved by, for example, mounting a heat lamp in location available for the dispensing stepper motor/lead screw assembly (using the same mounting screw holes).

The optical analysis can be done by placing a fiber optic emitter/detector in the stepper motor/lead screw assembly in place of a dispensing tube end. This will be stepped through the eight wells in the reaction mount just as the dispensing tip is. At each well, the detector could assess the status of the reaction. For example, by measuring color at the deblocking step in a nucleic acid synthesis, stepwise coupling efficiency can be established for each well. Other processes could be envisioned to be mounted at the stations in lieu of the dispensing motors. Moving, adding, deleting these processes is as easy as adjusting dispensing. Again, this increases the flexibility of this machine, making it capable of a variety of chemical protocols.

G. Containment System

The chemical protocol preferably takes place in an inert environment. Thus the airspace in which the process occurs (that around the rotating carousel) can be isolated in a containment chamber. In one embodiment, the containment is divided into two parts, an upper chamber and a lower chamber. The upper chamber is enclosed by a Plexiglas polygonal tube. Inside is the motor that turns the reaction disc and the dispensing station. This is all above the reaction disc. The lower chamber encloses the reaction disc itself, and the vacuum drain system, all inside a Plexiglas tube. The lower chamber is mounted on rails and is raised and lowered by a pneumatic cylinder. The lowered position allows operator access to the disc (for cleaning and removal of the product). In the raised position, the lower chamber is pressed against the bottom of the upper chamber forming a seal (using closed cell foam as the gasket material). The disc mates with the main motor and is in position for synthesis.

A non-reactive gas, such as nitrogen or argon, is pumped into the chamber from above and a regulator controls the inflow. A small outlet valve can be located on the bottom of the lower half of the chamber. This provides a constant flow of inert gas from above to below, pushing any chemical fumes away from the reaction wells. In addition, since all the electronics (motors) are located above the reaction disc, this ensures that no flammable fumes can diffuse up to where the motors are.

The majority of the inert gas that flows into the chamber leaves through the drain system. Since the drain is not continuously activated (but instead at every "step"), there is a discontinuous requirement for inert gas in the chamber. When the vacuum valve opens (e.g., every 15 seconds in a 24-station apparatus during nucleotide synthesis), it also will pull in a large volume of inert gas. To feed this gas flow through the vacuum system, and to avoid large pressure differences inside the chamber, a bellows system is attached to the chamber. When the drain is activated, the large volume of inert gas needed comes from the bellows, which contract. The inert gas inflow through the regulator is set such that when the drain is not active, the bellows expand to full size. An emergency relief valve is located on the bellows to avoid overpressure.

Since the efficiency of the coupling step of the synthesis is partly a function of temperature, the inert gas that flows into the chamber is preheated. This is done with a gas heater controlled by a PID controller along with a Drierite™ (WA Hammond Drierite) container that serves as a heat reservoir.

H. Programmable Computer

The apparatus also includes a programmable computer that controls the activity of all the systems. For example, a personal computer running an Intel Pentium processor running Windows 3.1 can control the entire machine. The control software can be written in C. The syringe pumps are controlled via RS-232 bus (serial port), all the valves for pneumatic and keeping the reagents stored under inert gas are controlled by a digital I/O board with its signals run through solid state relays. Motor control is done through motion controller cards.

Polymer synthesis, for example, can involve the addition of different monomer units to nascent polymers in each of the wells. In this way a library is created. The computer can be programmed to produce polymers of different specific sequences in each of the wells. This involves programming the computer to add a specific monomer to each well during each rotation. Thus, the computer must know what reaction mount is docked at a fluid delivery station that delivers a monomer, what rotation cycle is being carried out, and which delivery tube delivers which monomer.

III. Processes for Concurrent Chemicals Synthesis

This invention also provides a method for performing in parallel a series of physical steps in a chemical reaction protocol, wherein the protocol generates a chemical linkage on a parent molecule. The protocol can result in a linkage between a parent polymer and a monomer unit, such as a nucleotide in the production of nucleic acids, an amino acid in the production of polypeptides, a monosaccharide in the production of polysaccharides and analogs thereof. It also can result in the alteration of a parent scaffold molecule. For example, the alteration can be the generation of a new chemical linkage between the parent molecule and an exogenous component. The alteration also can be the modification of an existing linkage in the parent molecule, e.g., oxidation or reduction of existing bonds. Because the apparatus of this invention can be programmed to generate specific linkages in every well, the apparatus is well suited to the creation of libraries of compounds.

The method involves rotating the carousel step-wise for at least one full turn, and docking the reaction mounts at a station at each step. With each incremental step, a physical step in the protocol is performed on at least one well (preferably all the wells) of a plurality of reaction mounts (preferably all the reaction mounts) docked at the station. A rotation of the carousel results in the full series of physical steps being performed in each of the reaction wells. Thus, with every rotation of the carousel in which every station is in action, a new linkage is generated in the parent molecule attached to the solid support of a well. In this way, a polymer chain can be extended by the desired number of monomer units by rotating the carousel one time for each unit to be added.

For the following reasons, in performing the method of this invention, one will rotate the carousel through an initial rotation and a final rotation in order to initialize the wells and complete a cycle of the protocol in each well. Initialization is required in order to have the reaction stage of the molecules in every mount correspond to the station at which the mounts are docked. Completion is required in order to ensure that all the steps of the protocol are performed on the molecules of every reaction well.

The stations are arranged around the carousel in a sequence from the first station dedicated to performing a first step, to a last station dedicated to performing the last step. Because the stations are arranged in a circle, the last station is adjacent to the first station. Before the initial rotation, the parent molecules in all of the reaction wells are in the same state, prepared for the first step in the reaction. During the first rotation, the stations at which a reaction mount docks before the first station remain dormant during the docking: The first physical step is performed on a reaction mount only upon docking of the mount with the first station. Therefore, after the first complete rotation of the carousel, only first reaction mount, i.e., the mount initially docked at the first station, has had the entire process carried out on it. The second reaction mount has had all but the last step carried out, the third reaction mount has had all but the last two steps carried out, etc., until the last mount, which began at the second station, has had no steps performed on it. Thus, at the end of the first cycle, all the reaction mounts are initialized, with each mount prepared to have the next step carried out at the next station, but only the first mount having completed a cycle.

In order to complete each step of the protocol on the reaction mounts at some intermediate step of the reaction, the carousel must be rotated a final time. In the final rotation, no steps are carried out on the first reaction mount, which has already completed the cycle. Only the last step is performed on the second reaction mount. Only the last two steps are performed on the second reaction mount. All the steps are performed on the last reaction mount. Thus, by performing an initial and final cycle, each reaction mount has had all the physical steps performed on it once.

After the first cycle, the carousel can be rotated any number of intermediate cycles to add a new linkage to each of the reaction mounts during each cycle.

The practitioner may desire to create compounds with different numbers of linkages. For example, one may wish to prepare certain members of a nucleic acid library with 50 nucleotides and others with 40 nucleotides. The apparatus of this invention can accomplish this with proper programming. The method involves allowing a particular reaction well to sit out one or more intermediate cycles so that a linkage or linkages are not created in that particular parent molecule. Thus, entire reaction mounts or particular wells of a reaction mount can sit out any cycle.

Any chemical reaction protocol can be broken down into a number of physical steps by which the process is carried out. These steps include adding a liquid to a well, removing liquid from a well and waiting (incubate for a time, or a null step). Adding liquid to a well and removing it from the well can be combined at a single station to create a wash step. By properly arranging stations to perform these steps, and by adding appropriate liquids at appropriate steps, the reaction protocol can be carried out.

For example, phosphoramidite chemistry results in the creation of a phosphotriester linkage between a parent nucleic acid and a nucleotide, thereby adding a nucleotide to a parent polynucleotide chain. (The phosphodiester linkage is ultimately generated by removing protecting groups from the phosphate, generating a hydroxyl linkage.) A phosphoramidite chemistry protocol generally involves the following reaction steps: Deprotection of a protected sugar moiety on a parent nucleic acid; coupling of a protected nucleotide to the deprotected moiety to create a phosphite triester linkage; oxidation of the phosphite triester linkage to generate a phosphotriester linkage; and capping of unreacted nucleic acids. These reaction steps can, in turn, be dissembled into a number of physical steps. Stations can be arranged around the carousel to carry out these physical steps. In the case of an apparatus with 24 stations, certain of the stations can be dedicated to incubation or to washing a support more than once before proceeding to the next step. A washing station can be created by attaching a fluid delivery module at the station and attaching a vacuum line to the conduit connector at that station. In this example, the fluid delivery system includes several stations. Each station is connected to a supply of the appropriate liquid to be dispensed to the well.

Typically, polymers are built by the iterative addition of different monomers. For example, a DNA molecule will be comprised of the four bases, A, T, G and C (or other modified bases, such as I). Polypeptides will be comprised of the 20 naturally occurring amino acids, or other non-naturally occurring analogs. Thus, the fluid dispenser at a monomer dispensing station will include as many tubes as there are monomers. In the case of nucleic acids, this generally means four tubes, each of which dispenses one of the nucleotides. Alternatively, there could be four sequential stations, each dedicated to delivering one of the bases. In this arrangement, the other stations act as incubation stations when the particular nucleotide is not to be delivered to a well of the reaction mount. In the case of polypeptides, it may be necessary to dedicate several stations in sequence to the addition of various sub-sets of the 20 amino acids. In this case, certain of the stations will act as null stations if the particular amino acid is not delivered at that station. In preparing a library of nucleic acid or polypeptide molecules, the programmable computer will be programmed with the identity of all the sequences to be prepared. The computer will dispense the appropriate monomer to the appropriate well at the appropriate cycle.

The arrangement of stations to perform other chemical protocols is discussed in the Examples and will be apparent to one skilled in the art of solid phase chemical synthesis.

EXAMPLE

The following examples are presented by way of illustration, not limitation.

A. Introduction

All chemical protocols are divided into reaction steps which, in turn, are divided into the physical steps. The physical steps include delivering fluid to a well, draining fluid from a well, washing a well and incubating (wait or null step). Washing involves both adding fluid to a well and draining the fluid from the well. This can be performed in two sequential stations dedicated to fluid delivery and fluid draining, or by combining fluid delivery and fluid draining at the same station. More specifically, a fluid delivery module can be set up at the station and a vacuum line can be connected to engagement ports at the station. Incubation steps also can be adapted for heating, or analysis of the liquid (e.g., colorimetric). For example, a reaction step could involve adding liquid comprising a reactant to a well, incubating the well for a specified period of time defined by one or more incremental steps, draining the liquid from the well, and washing the well at least once.

Once all the reaction steps in the protocol are divided into physical steps, the number of steps is adjusted to the number of stations in the apparatus, e.g., 24, by the addition of appropriate wait steps or breaking a wash step into two steps (deliver liquid/drain liquid), for example. Then, the fluid delivery modules and vacuum lines are attached to the appropriate stations to carry out the physical steps in sequence. Then, the computer can be programmed to deliver the appropriate reactants to designated wells in designated cycles, so as to produce the desired chemical library. Also, the practitioner can add temperature control or liquid analysis steps as desired.

In one embodiment, the chemical library is a library of polymers. Presented here are chemical protocols and physical steps that one can perform on an apparatus of this invention to carry out the protocol.

B. DNA—Phosphite Triester Approach

DNA synthesis generally involves the steps of deprotection, condensation, oxidation and capping. In the phosphite-triester method, deprotection involves removing an acid-labile DMTr group from the 5'-OH of a sugar moiety. The condensation step involves coupling excess activated monomer to the growing chain. The oxidation step involves oxidation of 3'–5' internucleotide phosphite triester linkage to a more stable phosphotriester linkage. (After completion of the process, the polymers are treated to remove protecting groups, thereby generating the phophodiester linkages.) The capping step involves capping 5'-hydroxyl groups that failed to condense as acetate esters. This step is optional depending on how the cycle is optimized. When more than enough time is allowed for all of the reactions to proceed to completion, this step can be omitted. The general protocol can involve the following reaction steps:

1. washing the support;
2. dispensing a liquid comprising a deblocking agent to remove the protecting group;
3. draining the liquid comprising the deblocking agent;
4. washing the support;
5. dispensing a liquid comprising a coupling activator;
6. dispensing a liquid comprising a protected nucleotide;
7. draining the liquid comprising a protected nucleotide;
8. dispensing a liquid comprising a capping agent;
9. draining the liquid comprising the capping agent;
10. washing the support;
11. dispensing a liquid comprising an oxidizer; and
12. draining the liquid comprising the oxidizer.

Repeat steps 1–12 until nucleotide sequence complete

These reaction steps can be performed in the following physical steps. An apparatus of this invention was set up having 24 stations in the following arrangement. Each cycle of the carousel resulted in the addition of one nucleotide linkage to the parent nucleotide. The physical step indicates the system (fluid delivery/drain/null) to be dedicated to each station.

| Station: | Action: | Physical step: |
|---|---|---|
| 1 | Acetonitrile wash | 80 µL dispensed and drained |
| 2 | Acetonitrile wash | 80 µL dispensed and drained |
| 3 | TCA deblock | 40 µL dispensed |
| 4 | Drain | Drain |
| 5 | TCA deblock | 40 µL dispensed |
| 6 | Drain | Drain |
| 7 | Acetonitrile wash | 80 µL dispensed and drained |
| 8 | Acetonitrile wash | 80 µL dispensed and drained |
| 9 | Tetrazole Activator | 10 µL dispensed |
| 10 | Amidite | 10 µL of A,T,C, or G dispensed |
| 11 | 5' Special | 10 µL of AminoLink (or Null) |
| 12 | Incubate | Null |
| 13 | Incubate | Null |
| 14 | Incubate | Null |
| 15 | Incubate | Null |
| 16 | Incubate | Null |

| Station: | Action: | Physical step: |
|---|---|---|
| 17 | Drain | Drain |
| 18 | Acetonitrile wash | 80 μL dispensed and drained |
| 19 | Caps A and B | 12 μL of each Cap dispensed |
| 20 | Incubate | Null |
| 21 | Drain | Drain |
| 22 | Acetonitrile wash | 80 μL dispensed and drained |
| 23 | Oxidizer | 12 μL dispensed |
| 24 | Drain | Drain |

The above sequence is for synthesis of oligonucleotides. Other configurations are possible for other types of polymer synthesis. The step time in this example was 15 seconds, thus a full cycle of the disc requires about 6 minutes.

For synthesis of 50 mer oligos, the first 50 cycles involve the dispensing of one of the four amidites at each well throughout the synthesis. The 5 prime AminoLink is not used during these cycles, effectively being an incubation station. After the 50 mers are completed, another cycle can be done to attach a 5 prime aminolink. In this case, the standard amidites are used. In one particular protocol, the step time is increased to 20 seconds for the aminolink cycle to accommodate longer coupling time. Note that other monomers could be included in this system. They could be attached along with the standard amidites, or with a unique cycle if they require different timing.

The Teflon frits which serve as the substrate are round, 0.240 mm (just under 0.001") in thickness, and 7/32 inches in diameter. They are die cut from PerSeptive™ MemSyn sheets.

C. DNA—Phosphotriester Approach

In the phosphotriester approach to DNA synthesis, deprotection involves removing the acid-labile dimethoxytrityl (DMTr) or Pixyl (Px) group from the 5' hydroxyl (—OH). The condensation step involves condensing the monomer (as its triethylammonium salt) with the free 5'-hydroxyl group of the growing chain in the presence of a coupling agent and a catalyst. The oxidation step is not required since the phosphate moiety is already in the more stable form. The capping step is not necessary because there is an insignificant amount of unreacted 5' hydroxyl groups using the phosphotriester method. Note that for the washes in between the reaction steps, the phosphite-triester method uses acetonitrile (ACN), whereas the phosphotriester method uses pyridine and dichloroethane.

D. RNA

RNA synthesis is similar to DNA synthesis: it involves step-wise addition of a protected ribonucleoside phosphoramidite to the growing RNA chain that is attached to a solid support. For RNA synthesis, coupling takes much longer (~10 min) due to the extra protecting group on the 2'-OH of the ribose sugar. Therefore, additional incubation steps must be factored into the station arrangement. Otherwise, all of the steps in DNA and RNA syntheses—deprotection, condensation, oxidation, capping—are the same, employing the same reagents (except for the monomers and support-bound nucleosides). Therefore, the protocol for DNA synthesis can be followed to make RNA.

E. DNA and RNA Analogues

1. DNA/RNA hybrids

The practitioner can make DNA and RNA hybrids on the same instrument by supplying all of the appropriate monomers (A, T, C, G for DNA; A, U, C, G for RNA) and changing the coupling times depending on whether one is adding a deoxyribonucleoside or a ribonucleoside.

2. Backbone-modified nucleic acids

Backbone modifications to both DNA and RNA can be performed as well. Phosphorothioate oligonucleotides can be made simply by substituting the oxidizing reagent with a sulfurizing reagent (slightly increased delivery volume but same reaction timing). The cycle follows: 1) deprotection, 2) condensation, 3) sulfurization (with TETD, tetraethylthiuran disulfide in ACN), and 4) capping, with appropriate draining and washing in between each of the four steps.

Another method for backbone modifications uses H-phosphonate chemistry. The protocol can include the following steps:

1. Wash
2. Deblock (at least once)
3. Drain
4. Wash (at least once)
5. Couple (with 10 mM nucleoside H-phosphonate and activator)
6. Drain
7. Repeat steps 1–6 until nucleotide sequence complete*
8. Final deblock of entire nucleic acid (at least once)
9. Drain
10. Wash (at least once)
11. Oxidize ALL H-phosphonate bonds to phosphodiester linkages**
12. Drain
13. Wash (at least once).

*Capping is omitted since activator (pivaloyl chloride) also acts as capping reagent.
**Instead of oxidation with iodine, use alternative reagent to convert H-phosphonate bonds to phosphorothioates, phosphoramidites or phosphotriesters.

F. Polypeptides

The addition of amino acids onto a nascent polypeptide chain involves three chemical reactions: 1. Deprotection—protecting group (Fmoc or Boc) removed to make alpha-amino group on end of growing peptide chain available. 2. Coupling—amino acid residue is first activated into an active ester and then forms an amide bond with the deprotected alpha-amino group on end of growing peptide chain. 3. Capping [optional]—unreacted alpha-amino groups are capped with the same reagent used in DNA/RNA synthesis.

Two protocols exist for peptide synthesis, each named after the protection strategy. In Fmoc synthesis, the base-labile protecting group (Fmoc) is removed at each cycle. At the end of the synthesis, the side chain protecting groups are removed by a weak acid, which also cleaves the bond anchoring the peptide to the support. In Boc chemistry, the Boc protecting group is acid-labile and can be removed with a mild acid. A strong acid is used for the final deprotection and cleavage step. Fmoc chemistry is preferred due to the milder conditions (less caustic reagents).

A protocol for peptide synthesis using Fmoc chemistry can include the following steps:

1. Deprotect (at least once)—piperidine, 2×—7 minutes
2. Drain
3. Wash (at least once)—N-methylpyrrolidone (NMP) or dimethylformamide (DMF), 6×
4. Couple—18 seconds activation+35 minutes coupling
5. Drain
6. Cap [optional]—1 minute
7. Drain
8. Wash (at least once)—NMP or DMF, 3×.

Repeat steps 1–8 until amino acid sequence is complete.

A protocol for peptide synthesis using Boc chemistry can include the following steps:

1. Wash (at least once)—dichloromethane (DCM), 1×
2. Deprotect (at least once)—trifluoroacetic acid (TFA), 2×—6 minutes
3. Drain
4. Wash (at least once)—dichloromethane (DCM), 1×
5. Wash (at least once)—NMP or DMF, 6×
6. Couple—18 seconds activation+35 minutes coupling
7. Drain
8. Cap [optional]—1 minute
9. Drain
10. Wash (at least once)—NMP or DMF, 3×.

Repeat steps 1–10 until amino acid sequence is complete.

G. Peptide Nucleic Acids (PNA's)

PNA oligomer synthesis uses a modified solid-phase peptide synthesis protocol, similar to the Boc cycle above. Instead of coupling amino acid residues as in peptide synthesis, PNA monomers (A, C, G, T) containing the BOC protecting group are activated with a uronium salt activator. During synthesis, it is possible to modify the PNA oligomer with amino acids and various labels such as fluorescein, biotin or rhodamine.

A protocol for PNA synthesis using modified Boc chemistry can involve the following steps:

1. Wash (at least once)—dichloromethane (DCM), 1×
2. Deprotect (at least once)—trifluoroacetic acid (TFA), 2×—6 minutes
3. Drain
4. Wash (at least once)—dichloromethane (DCM), 3×
5. Wash (at least once)—NMP or DMF, 6×
6. Couple—1 minute activation+35 minutes coupling
7. Drain
8. Cap—1 minute
9. Drain
10. Wash (at least once)—NMP or DMF, 3×.

Repeat steps 1–10 until PNA sequence is complete.

The present invention provides novel materials and methods for concurrent chemical synthesis. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document Applicants do not admit that any particular reference is "prior art" to their invention.

What is claimed is:

1. An apparatus for synthesis of a polymer, the apparatus comprising:
    a) a rotatable carousel having an axis and comprising a plurality of reaction mounts each arranged on a radius with respect to the axis, each reaction mount comprising at least one reaction well having a drainage hole, wherein the drainage holes are connected to a liquid conduit and an exit port for each reaction mount;
    b) a rotator that rotates the carousel step-wise around the axis;
    c) a fluid delivery system for delivering a plurality of liquids comprising reagents useful in the synthesis of the polymer, the fluid delivery system comprising an assembly positioned above the carousel, the assembly comprising a plurality of dispensing modules, each dispensing module comprising a dispensing head adapted to deliver a predetermined amount of each liquid to each reaction well;
    d) a drain system comprising a plurality of drain lines, whereby the liquid in the reaction wells is drained through the drain lines by differential pressure;
    e) a conduit engagement means comprising a non-rotating connector plate positioned under the carousel, the connector plate having a plurality of engagement ports that are connected to the drain lines and are engagable with the exit ports, and an actuator that raises the connector plate to engage the engagement ports with the exit ports; and
    f) a programmable digital computer that controls the rotator, the fluid delivery system and the drain system.

2. The apparatus of claim 1, wherein the drain system is a vacuum drain system.

3. The apparatus of claim 1, wherein the number of reaction mounts equals the number of stations.

4. The apparatus of claim 1, wherein the carousel comprises 24 reaction mounts.

5. The apparatus of claim 1, wherein each reaction mount comprises 8 reaction wells.

6. The apparatus of claim 1, wherein the fluid delivery system delivers the liquid to at least one reaction well in each of at least three reaction mounts and the drain system drains the liquid from at least one reaction well of each of the three reaction mounts.

7. The apparatus of claim 1, further comprising a temperature controlling system that regulates the temperature of at least one reaction mount.

8. The apparatus of claim 1, further comprising an optical analyzing system that optically analyzes fluid in a well of at least one reaction mount.

9. The apparatus of claim 1, wherein each reaction mount comprises a plurality of wells and each dispensing module comprises a motor that moves the dispensing head to positions suitable for delivering fluid to each of the plurality of wells.

10. The apparatus of claim 1, wherein at least one station comprises both a dispensing module and an engagement port connected to a drain line.

11. The apparatus of claim 1, further comprising an airtight chamber that encloses the rotator, the dispensing assembly and the carousel.

12. The apparatus of claim 11, wherein the chamber comprises an upper chamber and a lower chamber wherein the upper chamber comprises the rotator and the dispensing assembly, and the lower chamber comprises the carousel, and wherein the lower chamber can be in a raised or lowered position with respect to the upper chamber, and wherein in the raised position, the chamber forms an airtight seal.

13. The apparatus of claim 12, comprising a regulator which regulates a directional flow of a gas to the upper chamber.

14. The apparatus of claim 13 further comprising a bellows connected to the regulator and to the upper chamber which functions as a reservoir for the gas.

15. The apparatus of claim 1, wherein at least one dispensing head is adapted to delivery a plurality of liquids.

16. A method of making a plurality of polymers by simultaneously chemically linking a plurality of monomers to a plurality of parent molecules, the method comprising:

(a) providing a rotatable carousel having an axis and comprising a plurality of reaction mounts each arranged on a radius with respect to the axis, each reaction mount comprising at least one reaction well comprising each of the plurality of parent molecules each parent molecule being attached to a solid support, and each reaction mount comprising at least one reaction well having a drainage hole for draining the reaction well by differential pressure, wherein the drainage holes are connected to a liquid conduit and an exit port for each reaction mount;

b) rotating the carousel step-wise around the axis a plurality of times, whereby each step docks each of the reaction mounts at each of a plurality of stations, wherein each station is dedicated to perform a step in the chemical linkage of the monomer to the parent molecule, whereby each monomer is chemically linked to each parent molecule.

17. The method of claim 16, wherein the parent molecule is cleavable from the solid support.

18. The method of claim 16, wherein there are 24 stations.

19. The method of claim 16, which is carried out in an inert atmosphere.

20. The method of claim 16, wherein the step in the chemical linkage is a washing step.

21. The method of claim 16, wherein the step in the chemical linkage comprises heating the reaction well.

22. The method of claim 16, wherein the step in the chemical linkage comprises include optically analyzing a well.

23. The method of claim 16, wherein the chemical linkage is selected from the group consisting of a phosphodiester bond, a phosphorothioate bond, a phosphonate bond, a phosphoramidate bond, an amide bond, an imine bond, a carbamate bond, an azo bond, a sulfone bond, a sulfonide bond, a sulfonamide bond, a sulfide bond, a disulfide bond, an ether bond, an ester bond, a thiourea bond, a urea bond and a carbon-carbon bond.

24. The method of claim 16, wherein the step of rotating is controlled by a programmable computer.

25. The method of claim 16, wherein the polymers are nucleic acids.

26. The method of claim 25, wherein the polymers are DNA.

27. The method of claim 25, wherein the polymers are RNA.

28. The method of claim 25 wherein the nucleic acid is coupled to a solid support in the well and the steps in the chemical linkage include, in sequence:
(i) washing the support;
(ii) dispensing a liquid comprising a deblocking agent to remove the protecting group;
(iii) draining the liquid comprising the deblocking agent;
(iv) washing the support;
(v) dispensing a liquid comprising a coupling activator;
(vi) dispensing a liquid comprising a protected nucleotide;
(vii) draining the liquid comprising a protected nucleotide;
(viii) dispensing a liquid comprising a capping agent;
(ix) draining the liquid comprising the capping agent;
(x) washing the support;
(xi) dispensing a liquid comprising an oxidizer; and
(xii) draining the liquid comprising the oxidizer.

29. The method of claim 25, wherein the monomer is a modified nucleotide comprising a minor groove binder.

30. The method of claim 16, wherein the polymers are peptide nucleic acids.

31. The method of claim 16, wherein the polymers are polypeptides.

* * * * *